US008452410B2

(12) United States Patent
Emborg et al.

(10) Patent No.: US 8,452,410 B2
(45) Date of Patent: May 28, 2013

(54) METHOD AND DEVICE FOR REFLEX-BASED FUNCTIONAL GAIT TRAINING

(75) Inventors: Jonas Emborg, Stenløse (DK); Ole Kæseler Andersen, Skørping (DK); Erika G. Spaich, Klarup (DK)

(73) Assignee: Aalborg Universitet, Aalborg Ø (DK)

( * ) Notice: Subject to any disclaimer, the term of this patent is extended or adjusted under 35 U.S.C. 154(b) by 119 days.

(21) Appl. No.: 12/876,783

(22) Filed: Sep. 7, 2010

(65) Prior Publication Data
US 2012/0059432 A1    Mar. 8, 2012

(51) Int. Cl.
*A61N 1/36* (2006.01)
(52) U.S. Cl.
USPC .................................................. 607/49
(58) Field of Classification Search
USPC .................................................. 607/49
See application file for complete search history.

(56) References Cited

U.S. PATENT DOCUMENTS

| | | | | |
|---|---|---|---|---|
| 3,881,496 | A * | 5/1975 | Vredenbregt et al. | 607/49 |
| 4,569,352 | A * | 2/1986 | Petrofsky et al. | 607/49 |
| 5,002,053 | A * | 3/1991 | Garcia-Rill et al. | 607/49 |
| 5,121,747 | A * | 6/1992 | Andrews | 607/2 |
| 5,674,262 | A * | 10/1997 | Tumey | 607/48 |
| 6,507,757 | B1 * | 1/2003 | Swain et al. | 607/49 |
| 2004/0173220 | A1 | 9/2004 | Harry et al. | |
| 2007/0173903 | A1* | 7/2007 | Goren et al. | 607/49 |

OTHER PUBLICATIONS

Emborg, Jonas "Modulation of the Nociceptive Withdrawal Reflex and its Use in Rehabilitation of Gait of Stroke Patients" PhD Thesis, Center for Sensory-Motor Interaction (SMI), Department of Health Science and Technology, Aalborg University, 2009.
Emborg, Jonas et al., "Withdrawal reflexes examined during human gait by ground reaction forces: site and gait phase dependency" Med Biol Eng Comput, 2009, pp. 29-39, vol. 47.
Emborg, J. et al., "Design and test of a novel closed-loop system tath exploits the nociceptive withdrawal reflex for swing phase support of the hemiparetic gait" Transactions on Biomedical Engineering, Aug. 2010.

(Continued)

*Primary Examiner* — Kennedy Schaetzle
(74) *Attorney, Agent, or Firm* — Knobbe Martens Olson & Bear LLP

(57) ABSTRACT

A device and method for gait training, such as for rehabilitation of a person after a stroke is provided. In some embodiments, the device comprises a stimulator, preferably electric stimulator, for provoking a spinal cord withdrawal reflex in the person by stimulation on the person's foot in response to a control signal. Hereby, the person's leg will move and initiate a gait swing. A sensor is placed to sense movement of the leg and provide a feedback signal accordingly. A processor unit with a processor runs a control algorithm which calculates the control signal in response to the feedback signal. Thus, the method is based on a closed-loop design, and the control signal is preferably calculated for each walking step, and it is preferably based on the feedback signal obtained from the preceding walking step. Hereby reflex habituation can be accounted for. Preferably, the stimulator has a plurality of stimulator channels with electrodes placed on different sites distributed on the sole of the foot and on the heel. The feedback signal may be based on accelerometer(s), and/or gyroscope(s), and/or goinometer(s) positioned on the leg and/or foot, e.g. partly or fully integrated in an in-sole for a shoe etc.

19 Claims, 5 Drawing Sheets

OTHER PUBLICATIONS

Emborg, J. et al., "A novel method exploiting the nociceptive withdrawal reflexes in rehabilitation of hemiplegic gait" World Congress on Medical Physics and Biomedical Engineering, Munich, Germany, Sep. 7-12, 2009, International Federation for Medical and Biological Engineering Proceedings, pp. 84-87.

Spaich, Erika G. et al., "Withdrawal reflex responses evoked by repetitive painful stimulation delivered on the sole of the foot during late stance: site, phase, and frequency modulation" Exp Brain Res, 2009, pp. 359-368, vol. 194.

Andersen, Ole K. et al., "Reflex receptive fields for human withdrawal reflexes elicited by non-painful and painful electrical stimulation of the foot sole" Clinical Neurophysiology, 2001, pp. 641-649, vol. 112.

Emborg, Jonas "Modulation of the nociceptive withdrawal reflex and its use in rehabilitation of gait of stroke patients" Center for Sensory-Motor Interaction (SMI), Aalborg University, Aalborg 2010, pp. 1-47.

International Search Report for PCT/DK2012/050171 dated Nov. 29, 2012.

Andersen, Ole K. et al., "Modular Organization of Human Leg Withdrawal Reflexes Elicited by Electrical Stimulation of the Foot Sole" Muscle Nerve, 1999, pp. 1520-1530, vol. 22.

* cited by examiner

METHOD AND DEVICE FOR REFLEX-BASED FUNCTIONAL GAIT TRAINING

FIELD OF THE INVENTION

The invention relates to the field of devices and methods for functional therapy for patient suffering from a disorder causing gait problems, such as patients suffering from stroke that inhibits or eliminates the patient's gait ability. Especially, the invention relates to functional electrical therapy.

BACKGROUND OF THE INVENTION

Patients that suffer from a gait disorder, e.g. patients being partially or completely immobile due to a hemiparetic condition caused by a stroke or traumatic brain injury, which has resulted in damage of an area of their brain, have a significant better chance of rehabilitation if intensive gait training is initiated within 3 months after the stroke. In this early period, the brain is especially suited to regenerate/relearn the ability to control the muscles, if the sufficient sensory, learning input is provided, i.e. by completing functionally adequate gait training. However, such gait training is often impossible for the patient without help, if the brain area controlling the leg muscles is completely damaged and thus unable to generate appropriate motor control nerve signals in the normal way to make the patient walk.

The necessary electrical nerve signals to the leg muscles causing the patient to walk can be synthesized by means of a computer or processor that generates synthesized electric signals to each group of muscles in the leg(s) in the right sequence via a large number of implanted electrodes or cutaneously mounted electrodes. Such systems are used for patients suffering from injuries in the spinal cord, i.e. patients with a permanent interruption of nerve signals between the brain and the legs. A less complex example of such synthesized gait aid is an electronic device that helps patients suffering from the drop foot syndrome.

However, for patients suffering from a stroke, the gait impairment is often of a permanent character even though many patients manage to walk by learning compensatory movements to move the paretic limb forward. In particular lifting the leg by flexing the hip in the swing phase is difficult. To relearn the gait function intense physiotherapy in the subacute phase is critical. Electrical stimulation to support production of the swing phase is suggested, which will allows extended daily physiotherapy and more functional walking capability. For daily therapy for in-patients stimulation of multiple muscles via several electrodes, as used in existing devices or systems, are far too time consuming to mount and take off in relation to daily physiotherapy. Moreover, direct stimulation of hip flexor muscles are difficult due to the deep location of these muscles.

SUMMARY OF THE INVENTION

Therefore, following the above description, there is a need for a device and a method of therapy to help rehabilitation of patients suffering from a stroke and thus temporarily needs assistance to be able to perform gait training. The device should be easy to mount and take off, in order to be efficient in practical therapy so as to utilize the time spent by physiotherapeutic personal for the vital gait training of the patient, and not for struggling with the equipment related to the training.

In a first aspect, the invention provides a device arranged for gait training, such as for rehabilitation of a person after a stroke, the device comprising:

a stimulator arranged to generate a stimulation on the person's foot in response to a control signal, wherein the stimulation is arranged to provoke a spinal cord withdrawal reflex in the person so as to cause the person's leg to move, a sensor arranged to sense a parameter representative of a movement, such as position, acceleration, velocity, of the person's leg and to generate a feedback signal accordingly, and a processor unit operationally connected to the stimulator and the sensor, the processor unit comprising a processor running a control algorithm so as to generate the control signal in response to the feedback signal.

Such a device is highly suited for gait rehabilitation therapy of post-stroke hemiparetic patients, since the person's own normally functioning nociceptive withdrawal reflex (NWR) is triggered by stimulation of the foot, thus causing the spinal cord to generate a reflex in the form of integrated motor nerve signals leading to adequate contraction of many muscles in the leg that make the person move his/her leg upward and forward and thus initiate the swing phase during walking. Even though this stereotyped flexion can be considered to provide an uncontrollable leg movement, it has been shown in experiments that suitable control of the stimulation, such as proper control us stimulation site, stimulation intensity, stimulation timing, stimulation duration, and stimulation frequency in response to the feedback signal it is possible to evoke suitable hip, knee and ankle movement to allow a functional gait cycle, which would otherwise be impossible for a hemiparetic patient. Thus, the use of a closed-loop control system in the generation of the electrical stimulation allows a quality of gait which is acceptable for gait training. This approach enables sufficient learning input to the brain to be able to regenerate its gait control function and thus significantly improve the patient's chance of completely restoring the patient's ability to walk and thus generally increase the patient's quality of life.

With the closed loop configuration provided by the feedback signal, e.g. representing an angle of the knee or another feedback parameter, the control algorithm can be designed to optimize the gait by adjusting different parameters of the stimulation, e.g. stimulus intensity or stimulation site on the foot for each walking step and/or selection of stimulation timing (phase of the gait cycle), such as selection of a suitable stimulation of more stimulation sites versus time during the gait cycle. Hereby, it is possible to avoid or at least suppress reflex habituation effects and thus maintain a high quality of gait during several walking steps and thereby follow a predetermined target trajectory. Even though the rather powerful stimulation required is perceived as painful, the patient has a positive experience with such device, since the patient has the feeling of walking by their own effort and a perception of rapid improvement of their walking performance. As will be explained in more detail below, the required stimulation can be implemented with only few units with rapid donning and doffing, and thus save time that can be spent for the actual gait training. Hereby the device is suited for physiotherapy clinics, hospitals or rehabilitation centres etc.

In some embodiments, the stimulator comprises an electric stimulator arranged to generate an electric stimulation on the person's foot to provoke the spinal cord withdrawal reflex. In a preferred embodiment, the stimulator can generate a sufficient electric current to induce a withdrawal reaction via cutaneously applied electrodes on multiple sites on the person's foot. Electric stimulation is advantageous, since the intensity can rather easily be adjusted by adjusting the applied current and stimulus duration. However, it is to be understood that other types of stimulation on the foot can be used to cause the withdrawal reflex.

The control algorithm may be arranged to vary the control signal in response to the feedback signal so as to optimize gait quality, e.g. the control algorithm may be arranged to optimize the gait by adjusting the control signal and thus the stimulation so as to follow a target trajectory for the gait. This may be in the form of knee angle versus time during one walking step, in case the feedback from the sensor includes a continuous representation of the knee angle of the person's leg. Also, the precise stimulation timing during the step cycle can be adjusted in response to the feedback signal in order to optimize gait quality.

The stimulator preferably comprises a plurality of individually controllable stimulation channels spatially distributed to provide stimulation on different sites on the person's foot. Such plurality of individually controllable channels may be in the form of spatially distributed electric electrodes connected to individually controllable control channels, either controllable via one common control signal or in parallel control signals. The stimulator may especially comprise at least a channel arranged to stimulate the posterior side of the heel and a channel arranged to stimulate a position on the sole of the foot. Especially, stimulation on the heel provokes a reflex in the form of a forward movement of the leg which is critical for forward propulsion. More specifically, the stimulator may comprise a plurality of stimulators arranged to stimulate different positions on the person's foot. Moreover, it is possible, for each walking step to switch to another stimulation position and thereby avoid or at least suppress habituation to one stimulation position. Furthermore, the quality of gait can be refined by combining stimulation at several stimulation positions at the correct timing during the step cycle. E.g. a heel stimulation to initiate the swing followed by a stimulation of a distal part of the sole of the foot so as to provoke an upward bending (dorsi flexion) of the foot.

The control algorithm and the stimulator are preferably arranged to vary at least one of: stimulation intensity, stimulation duration, and stimulation timing in response to the gait cycle measured by the feedback signal. Most preferably, the control algorithm and stimulator are arranged to vary more of these parameters in response to the feedback signal at least stimulation duration and stimulation position on the foot, so as to adapt stimulation to habituation effects, e.g. for optimizing gait with respect to a target trajectory. The control algorithm may be arranged to generate the control signal in response to the feedback signal by selecting between one of a plurality of predetermined stimulation options. Such plurality of stimulation options may comprise stimulation options with different stimulation intensities, different stimulation durations, and different stimulation positions (sites). The selection between the predetermined options may be performed between a number of predefined sets of stimulation parameters stored in memory, and wherein each of said predefined sets of stimulation parameters have been evaluated with respect to a target measure, thus allowing a selection based on this target measure.

Preferably, to take into account habituation and gait quality, the processor unit is arranged to calculate the control signal for each walking step of the person. Preferably, the control signal for one walking step is calculated based on the feedback signal received during at least one previous walking step, such as during the preceding walking step. More specifically, the control algorithm may be arranged to calculate an estimated deviation from a predetermined target trajectory for a walking step based on the feedback signal from at least one previous walking step.

The stimulator may be arranged to generate a stimulation burst comprising a plurality of stimulations of a stimulation duration, such as less than or equal to about 5 stimulations of a stimulation duration of less than or equal to about 1 ms with an inter-stimulus interval of less than or equal to about 4 ms (e.g., less than or equal to about 5, 4, 3, 2, or 1 stimulation of a stimulation duration of less than or equal to about 1, 0.75, 0.5, 0.25, or 0.1 ms with an inter-stimulus interval of less than or equal to about 4, 3, 2, or 1 ms). Especially preferred embodiments are configured such that the stimulator is arranged to generate a stimulation sequence of a plurality of stimulation bursts, such as a sequence of about 4 stimulation bursts. To adjust stimulation intensity, it is possible to vary one or more of: current amplitude, the number of stimulations in a burst, stimulation duration, inter-stimulus interval, and the number of stimulations in one sequence. Some of such sequences of stimulation bursts have been experimentally found to be suitable.

The sensor may comprise at least one of: a sensor arranged to sense an angle of the person's knee, a sensor arranged to sense a distance between the person's foot and the ground below the foot, one or more contacts arranged to sense if the person's foot touches the ground. Preferably, the sensor is arranged to generate a continuous feedback signal, or at least a sampled feedback signal allowing a sufficiently precise tracking of the person's leg during one walking step. E.g. the sensor may comprise two or more different types of separate sensors, so as to allow a feedback signal with a more precise tracking of the gait. E.g. the sensor may include an angular sensor to sense a knee angle, and a contact under the foot to sense when the foot touches the ground. The sensor may comprise one or more angular sensors to sense an angle of the hip, knee, and ankle. Alternatively, or additionally, the sensor comprises: an accelerometer positioned to sense a movement of the person's foot or leg, a gyroscope arranged to sense a change in position or angle of parts of the leg, e.g. joints, and a tilt sensor. One or more of these sensor elements may be built into a sock or shoe so as to eliminate the need for an individual mounting procedure.

In order to provide a therapy device with short donning/doffing time, the stimulator or at least a part of the stimulator, e.g. stimulator electrode(s), may be mounted in a footwear or part of the footwear, such as a sock or an insole for a shoe, so as to facilitate mounting of the stimulator on the person's foot. Especially, electric electrodes may be mounted in a foot sole at different positions so as to be able to electrically stimulate different positions on the foot, (e.g. at least one heel position and 3, 4, or 5 positions distributed in a length direction on the foot sole). The sensor may additionally or alternatively be mounted in said footwear, such as in the form of a contact to sense if the foot touches the ground, or in the form of a laser device or ultrasonic device arranged to measure a distance between the foot and the ground, and/or in the form of one or more accelerometers.

The processor unit may be implemented as a portable unit, such as a portable unit arranged for carrying by the person, such as arranged for attachment to a part of the person clothes, e.g. adapted for mounting in a person's belt.

To be suited for persons with both legs paralyzed, the device may comprise a second stimulator arranged for stimulation on the person's opposite foot, and a second sensor arranged to sense a second parameter representative of a position of the person's opposite leg, and wherein the processor unit is arranged to generate a second control signal to the second stimulator in response to a second feedback signal from the second sensor, so as to provoke movement of both legs of the person.

In a second aspect, the invention provides a method of rehabilitation therapy of a gait impaired patient, such as a patient suffering from a stroke, the method comprising:

sensing a parameter representative of a position of the person's leg, and applying a simulation on the person's foot in order to provoke a spinal cord withdrawal reflex causing the person's leg to move, wherein the stimulation is determined in response to said parameter representative of the position of the person's leg.

In a third aspect, the invention provides a computer executable program code arranged to cause a computer device to generate a control signal to a stimulator in response to a feedback signal from a sensor so as to perform the method according to the second aspect.

It is appreciated that the same advantages and equivalent embodiments apply for the second and third aspects as mentioned for the first aspect.

BRIEF DESCRIPTION OF THE DRAWINGS

Embodiments of the invention will be described, by way of example only, with reference to the drawings.

DETAILED DESCRIPTION

Figure 1:
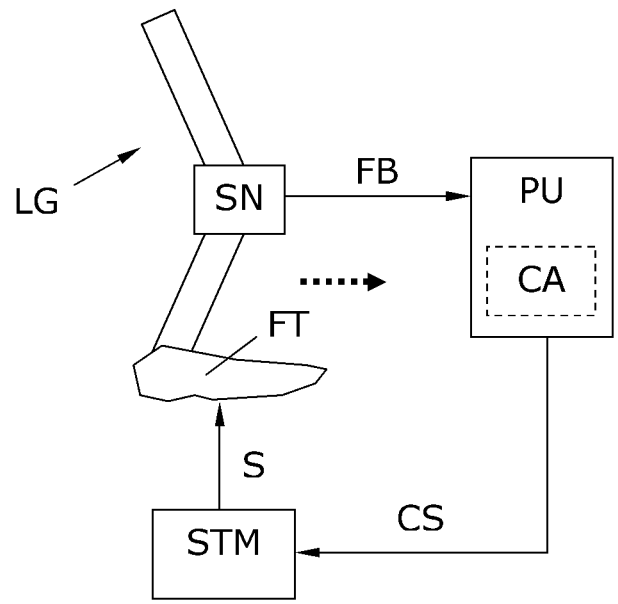
FIG. 1 illustrates basic parts of a simple therapy device embodiment.

FIG. 1 shows schematically the leg LG and foot FT of a person together with basic parts of a therapy device embodiment according to the invention. The device includes a stimulator STM arranged to apply a stimulation S on the foot FT with the purpose of provoking the person's withdrawal reflex, thus causing the leg LG to move and thus initiate swing phase. Such stimulation S of course requires an intensity to trigger the withdrawal reflex, and typically the required intensity is perceived as less pleasant. The stimulator STM is controlled in response to a control signal CS generated by a processor unit PU which runs a control algorithm CA. This control algorithm CA calculated the control signal CS in response to a feedback signal FB which the processor unit PU receives from a sensor SN which is arranged to sense a parameter, e.g. acceleration of the leg LG, here illustrated as a goniometer sensing the knee angle, and generates the feedback signal FB according to this parameter. The control algorithm CA is preferably designed to adjust the control signal CS so as to obtain a target trajectory for the leg LG. In the illustrated example, the control algorithm CA may be designed to determine a control signal CS resulting in a stimulation S that would most probably provide a target knee angle of the leg LG as a function of time during one walking step.

The sensor SN may in addition to or as an alternative to a goniometer include a simple contact or switch mounted to sense if the foot FT touches the ground, thus providing valuable position for the control algorithm CA with respect to determining when a gait cycle is initiated. It is to be understood that several sensor types may be used to derive a feedback signal which represents a parameter describing the position and/or movement of the leg during the gait. This could be accelerometers, tiltsensors and gyroscopes that are used for estimating the position of the leg and thereby joint angles. E.g. a camera can be used to capture digital images of the leg during the patient walking. Via appropriate image analysis processing on the image, a suitable feedback can be derived, e.g. in the form of one or more of hip, knee, and ankle joint angles and foot distance to ground, or in the form of a more complex parametric description of the leg movement.

Preferably, the stimulation S is an electric stimulation which has the form of electric current bursts of 5 pulses with a duration of 1 ms, with inter-stimulus intervals of 4 ms. Sequences of 4 such bursts have been found to be optimal, however it is to be understood that all of these stimulation parameters may be varied in order to obtain an optimum gait quality, taking into account reflex habituation effects. The electrode impedance is known to vary significantly over time, and thus it is preferred that electric stimulations with a constant current are used. This helps to provide a stimulation S which is independent on the actual electrode impedance and thus controllable. However, it is preferred that the amplitude of the stimulation S can be varied on purpose so as to adapt the stimulation S intensity to the sensed feedback.

Figure 2:
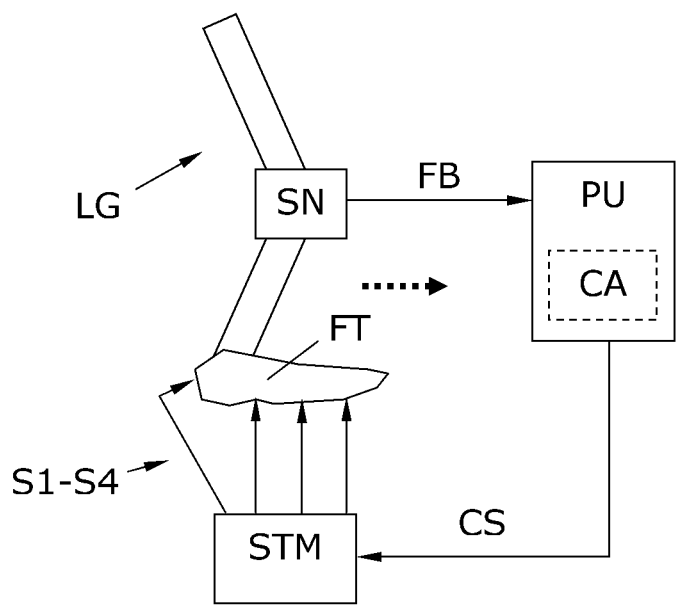
FIG. 2 illustrates basic parts of a therapy device embodiment with a plurality of simulation channels.

FIG. 2 also shows a sketch of a therapy device embodiment. This embodiment differs from the one in FIG. 1 in that the stimulator STM includes a plurality, here four, separate stimulator channels and associated electrodes. The stimulator channels are spatially distributed so as to be able to apply four separate stimulations S1-S4 at different positions on the foot FT. As illustrated, one stimulation position is on the posterior heel, while the remaining three positions are different position on the sole of the foot, spatially distributed in a length direction of the foot FT. Especially, the heel position can be used to initiate a forward swing of the leg LG, while a distal part of the sole of the foot can be used to cause a dorsi flexion of the foot FT ensuring ground clearance during the swing phase. Hereby, the control algorithm CA can be designed such that an optimal gait can be obtained by appropriately determining a control signal CS that selects to stimulate the foot FT appropriately by one or more of the stimulations S1-S4, and especially the stimulations S1-S4 should be applied at the most optimal time during the step cycle. To do so, the control algorithm CA may be arranged to select between a fixed number of different predefined stimulation scenarios, e.g. by calculating for each predefined scenarios an estimated mean square error from a target trajectory, and thus selecting the scenario with the lowest mean square deviation.

The plurality of stimulations S1-S4 at different positions can be used to reduce habituation effects, i.e. reduce the effect that several stimulations at one position causes a reduced reflex response, or no reflex response at all. Especially, it has been found that the habituation can be "reset" by one high intensity stimulation at another position or site on the foot FT, thus causing the reflex response to return to normal. Such monitoring for habituation by monitoring the feedback signal FB and appropriate shift in stimulation position is preferably implemented in the control algorithm CA.

Figure 3:
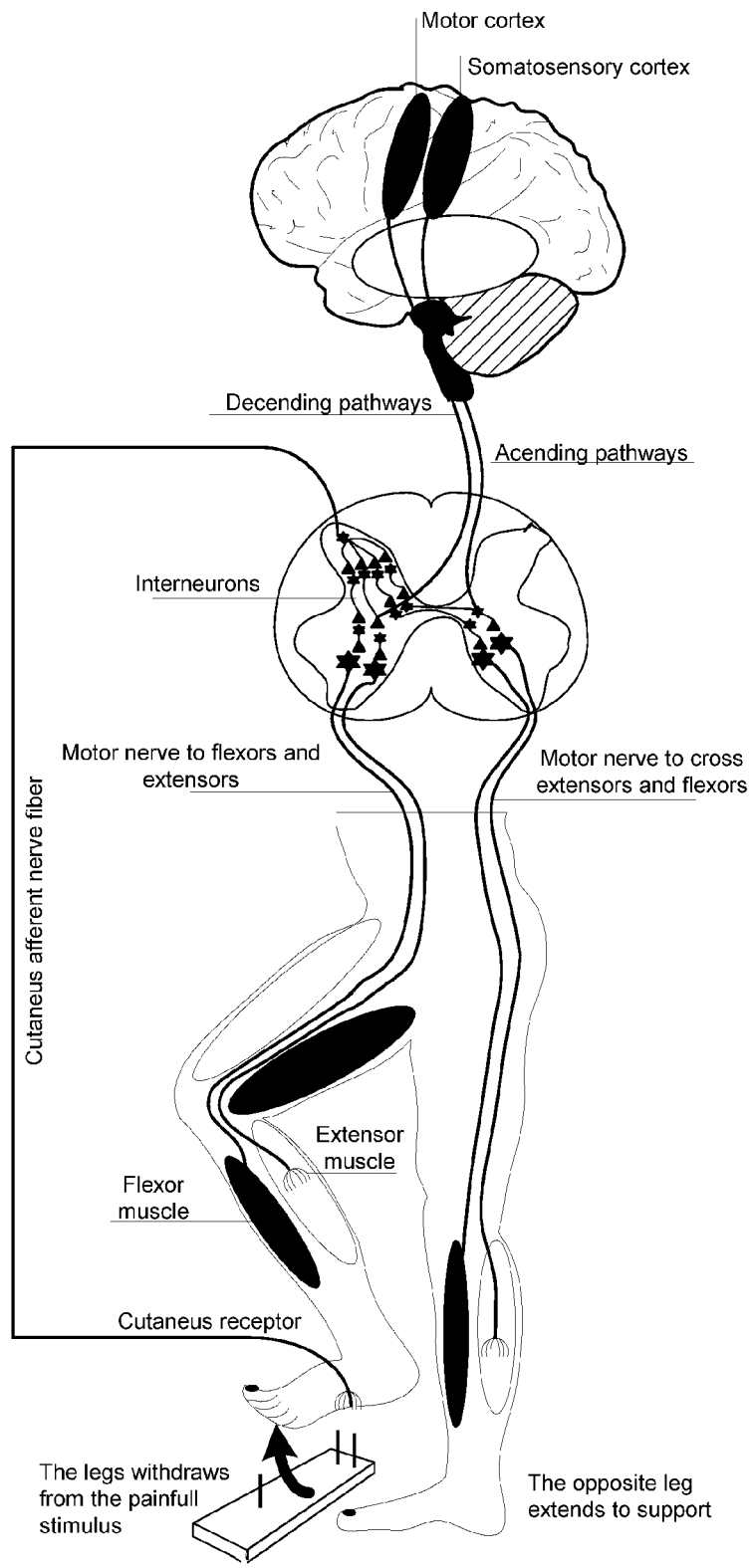
FIG. 3 illustrates the principle of the human spinal cord withdrawal reflex upon application of a stimulation of the foot.

FIG. 3 illustrates a basic principle which is utilized in aspects of the invention, namely the provoked stimulation of the NWR, i.e. the spinal cord reflex pathway which causes activation of multiple muscles in a person's leg to withdraw the leg in response to a painful stimulation. This reflex is possible to provoke in a person suffering from a stroke, and thus cause a leg movement which can be used in gait training, even though the person is unable to move the leg voluntarily due to damage to supraspinal motor pathways. The muscle control, which is still functioning in the spinal cord is utilized to activate leg muscles. Early gait training is a vital part of therapy after a stroke, as full or partial recovery of gait function is most efficiently obtained by early applying the brain with appropriate sensory feedback during persistent gait training. This early gait training thus enables the brain to automatically spatially rearrange the motor control associated with walking and thus restore the ability of walking.

Even though the reflex may be considered to be a stereotyped reflex, it has been found that the human lower limb nociceptive withdrawal reflex elicited by painful electrical stimulation of the sole of the foot depends strongly on the stimulation site. If stimulation is applied to the forefoot this will primarily evoke ankle dorsiflexion through tibialis anterior activation. If the stimulation is applied to the heel, it primarily evokes ankle plantar flexion via soleus activation. Activation of hip flexors can be achieved for any stimulation site on the sole of the foot and is substantially modulated during the gait cycle. This is preferably utilized in gait therapy, which therefore preferably includes a plurality of stimulation positions.

Figure 4:
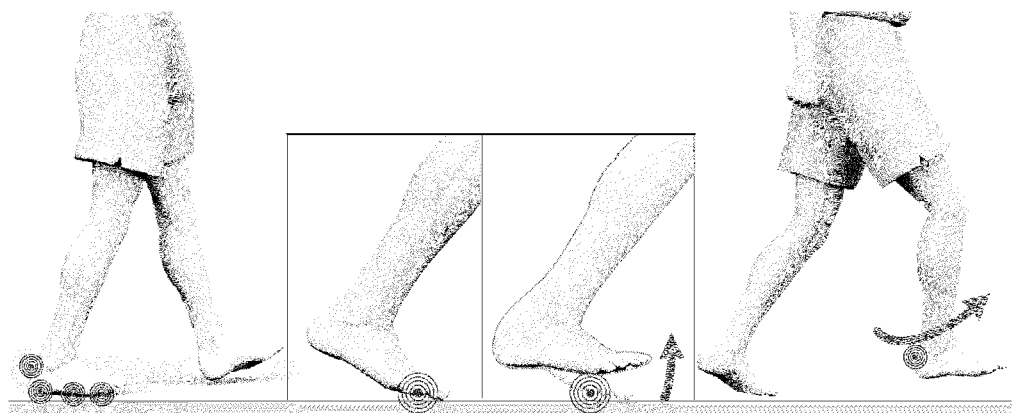
FIG. 4 illustrates different stimulation positions on the foot and the associated periods during the step cycle where these positions are preferably stimulated.

FIG. 4 illustrates four basic phases of a gait cycle and the use of four different stimulation positions on the foot to be used at different periods during the gait cycle. To initiate a leg swing, at least stimulation on the heel is preferred, but more foot sole positions may be used in addition or alternatively to ensure ground clearance during the swing phase. When the forefoot hits the ground, stimulation of the frontal part of the foot sole may be initiated in order to cause an upward flexing of the foot. Typically it is not possible to obtain such upward flexing of the foot in response to a sensor signal, i.e. with close-loop feedback, since the delay in the reflex is too large. However, it is possible to simulate different positions or times during a walking step where such upward bending of the foot can be utilized and thus stimulation of this reflex may form part of the total stimulation during a walking step.

Figure 5:
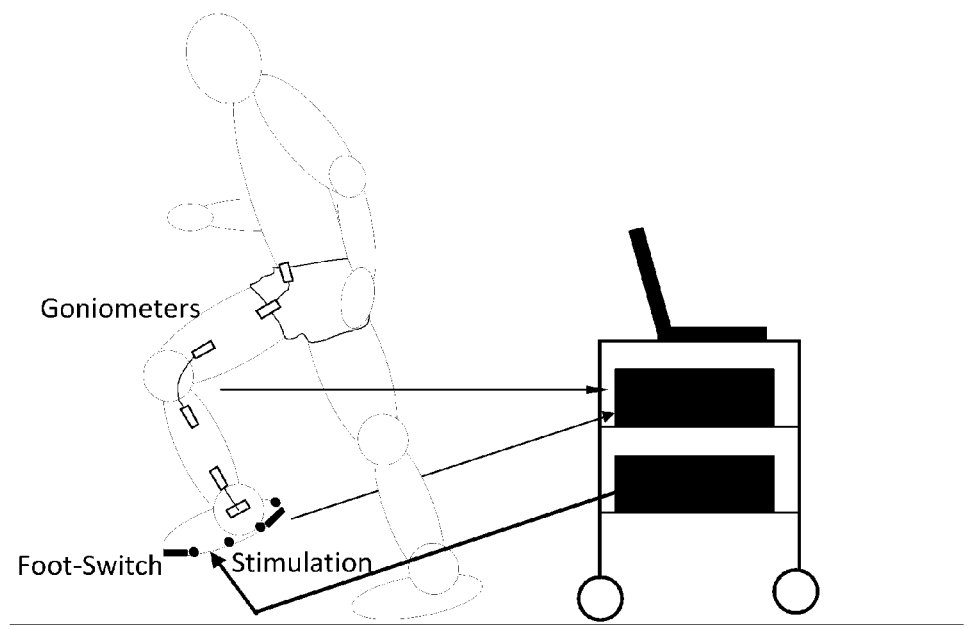
FIG. 5-7 illustrate three different therapy device implementations.
Figure 6:
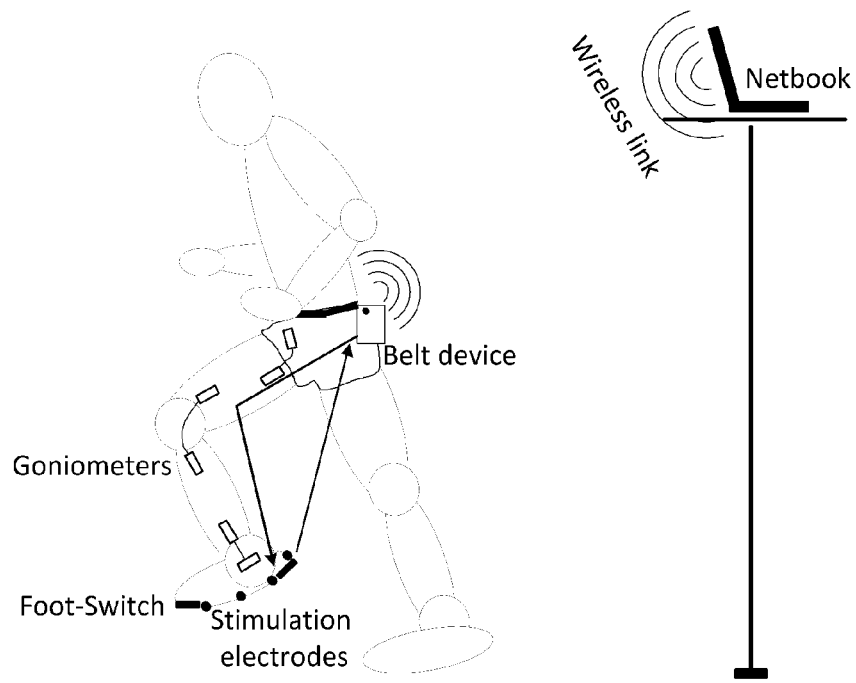
Figure 7:
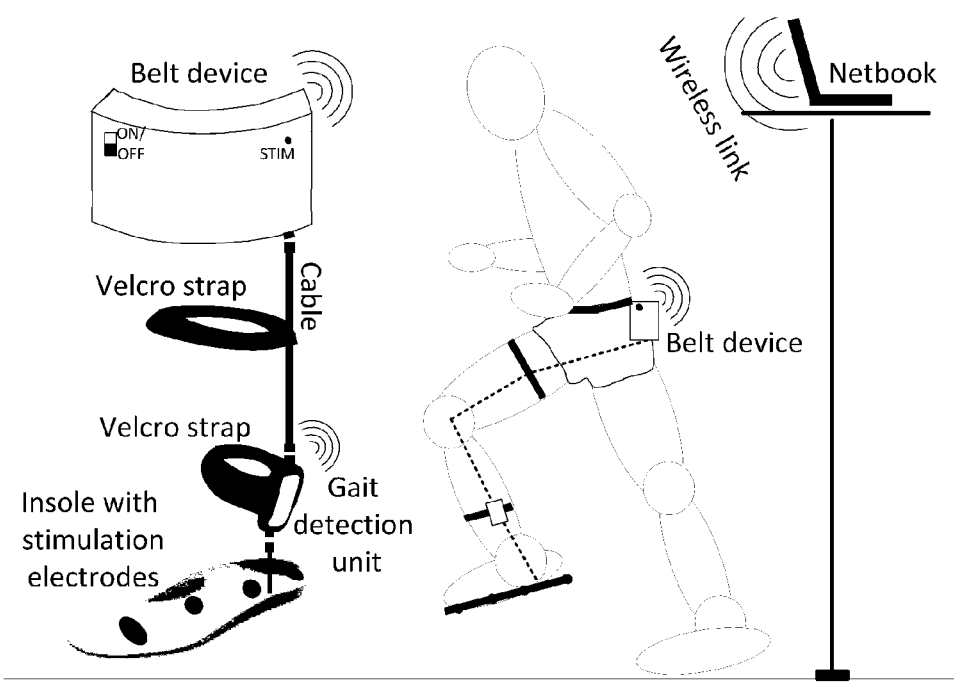

FIGS. 5-7 sketch different therapy device implementations suitable for rehabilitation of a patient since the embodiments allow easy mounting and easy removing. Thus, the embodiments are suited for normal therapy situations with a rather limited total time available for therapy of each patient. The simple mounting thus allow high utilization for the actual gait training of the patient with a limited waste of time spent on the therapy equipment.

FIG. 5 illustrates an embodiment where the sensor system includes separate hip, knee, and ankle goniometers and a foot switch to sense when the foot is in contact with the ground. Separate switches may be used to sense when the fore foot and heel are in contact with the ground, thus enabling sensing both when the foot touches the ground, and when the foot leaves the ground. Preferably, the sensor placed on the person's ankle includes an accelerometer and/or gyroscope the sense additional parameters related to the movement of the person's leg during a walking step.

The stimulator can be an electric stimulator with less than or equal to about 4 stimulation electrodes: e.g., one electrode to stimulate the posterior heel, and 3 electrodes to stimulate three different positions on the sole of the foot. The processor unit is implemented with a computer, e.g. a notebook PC, which is connected to an input interface unit serving to interface the sensors. Further, the computer is connected to the stimulator in the form of an output interface which generates the electric signals to the electrodes. The control algorithm is implemented in software which is executed on the computer.

FIG. 6 illustrates an embodiment with the same sensors and stimulators as the embodiment of FIG. 5, however here a portable device in the form of a battery driven device placed on the belt includes hardware to interface the sensors and to generate the electric signals to the stimulators. The belt device communicates with a computer, e.g. a notebook PC, via a wireless link. The control algorithm is then run on the computer, as already described for FIG. 5. The belt device thus communicates the feedback signal via the wireless link to the computer and receives in response a control signal which it translates into electric signal(s) which is applied to the appropriate one(s) of the electrodes.

FIG. 7 illustrates yet another embodiment which in its basic structure is similar to the one shown in FIG. 6. However, as illustrated, the sensor is here implemented as a gait detection unit which, e.g. by means of one or more accelerometers and/or gyroscopes, tiltsensors, that generates a feedback signal which is wirelessly transmitted to the belt device or directly to the computer. The belt device is connected to the stimulation electrodes by means of a cable which is attached to the patient's leg by means of a Velctro™ strap. Such Velctro™ strap is also used to attach the gait detection unit to the lower leg of the patient. Alternatively, the gait detection unit may be attached to the patient's shoe. The stimulation electrodes are seen to be placed in an insole suited to fit into the patient's own shoe or into a dedicated training shoe. The electrodes are placed in the upper surface of the insole so as to allow direct contact with the skin on the foot sole and heel of the patient. Preferably, the insole is adhesive to the sole of the foot so as to ensure proper electrode contact.

It is to be understood that in all the illustrated embodiments, goniometers may be entirely replaced by sensor(s) in the form of accelerometer(s) and/or gyroscope(s). Especially, it may be preferred to build in such accelerometer(s) into a part of an in-sole.

Figure 8:
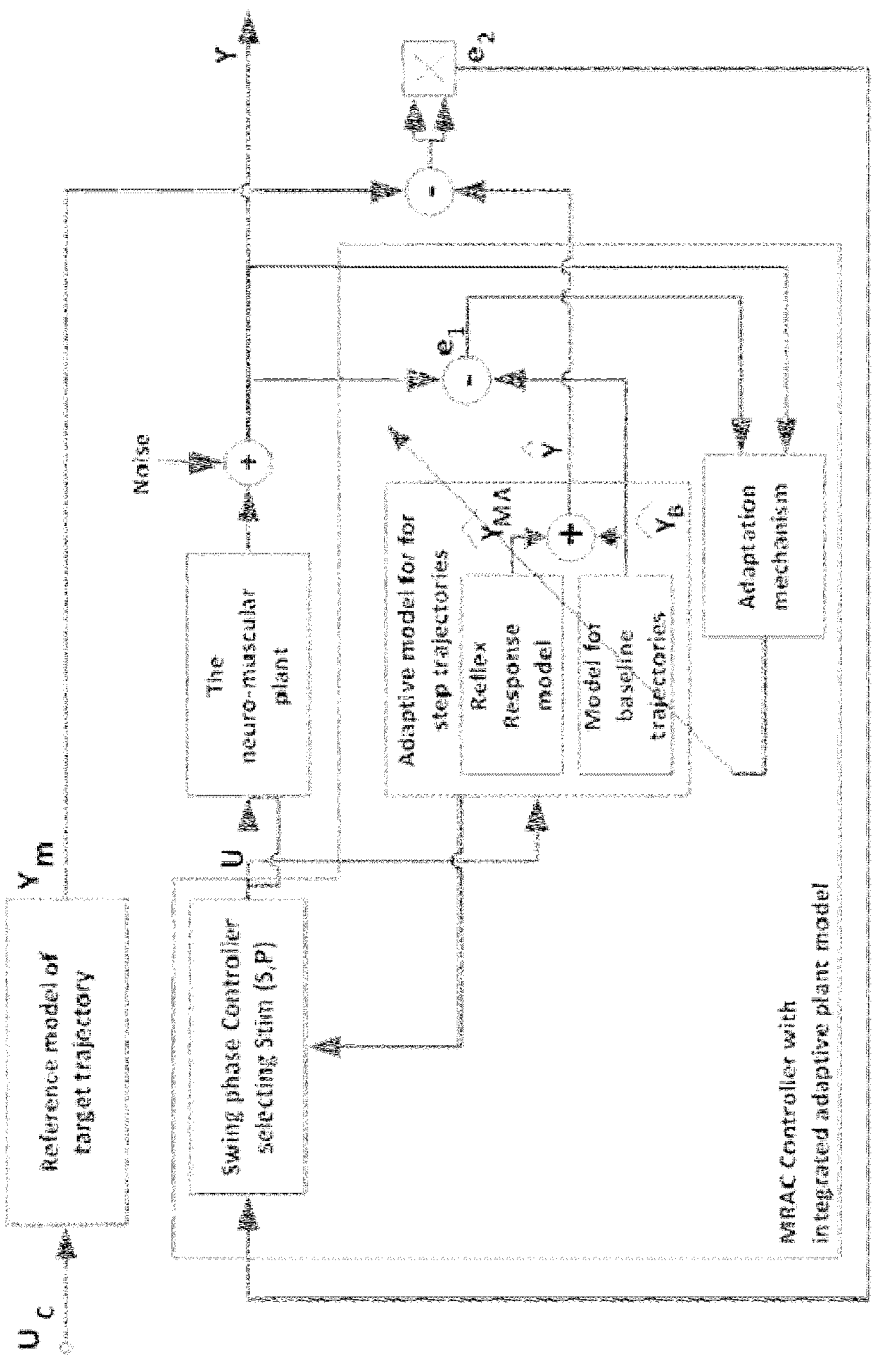
FIG. 8 illustrates the principles of a suitable control algorithm.

FIG. 8 shows in schematic form an implementation of a control algorithm which can be regarded as a modified Model Reference Adaptive Control system (MRAC). Conventional MRAC concepts are associated with parametric models, but in this application neither model structure nor parameter values are known. Instead, a novel modified MRAC method is introduced, in which models of entire kinematic trajectories ($\hat{Y}$) in the heel-off phase are recursively derived from input-output data for three joint angles (hip, knee, and ankle) obtained from physical sensors or estimated from alternative sensor signals. Such alternative sensor signal may be input from one or more or a gyroscope, a accelerometer, or a tilt sensor which is used to calculate a position of the leg, e.g. in the form or one or more a joint angles based on these sensor inputs. Based on the kinematic trajectory model, the controller continuously compares the deviation of the present step to a target trajectory. The controller minimizes the error $e_2$ between the predicted output and the target trajectory. Changes in the baseline gait pattern or in the reflex response induces changes in a plant model implicitly embedded in the MRAC controller. The controller then predicts all outcome possibilities and chose the combination of Intensity, Duration, Site and Phase that results in the lowest error; the embedded plant model forces thereby the adaptive controller to change the stimulation parameters, if needed.

The MRAC strategy includes: specification of a reference model with the desired dynamics and on-line parameter estimation. The system comprises an ordinary feedback loop composed of process and controller. The error ($e_2$) is the squared difference between the predicted outputs of the system (Y) and the reference model ($Y_m$). There are two loops in the system: an inner loop, which provided the ordinary control feedback and an outer loop, which adjusts the parameters in the inner loop. Thus, the aim for the closed-loop system is to follow the reference model trajectory $Y_m$, while the neuromuscular plant model is described by $\hat{Y}$.

The use of trajectories, rather than parameterized dynamical input-output models, is stressed by the use of the symbol $\mathcal{S}$ for the individual coordinates.

The dynamics of the outer loop, which adjusted the controller parameters, is normally assumed to be slower than the inner loop and the adjustments are often based on a gradient approach. However, since a parametric model is not available for the present system, the gradient approach is deemed infeasible. It is crucial to reflect gait improvement, habituation, and fatigue as well as to reduce noise from normal step-to-step variability. This is achieved by introducing a simple moving average (MA) approach for modeling the kinematic reflex responses trajectory, where the length of the MA-filter reflects the adaptation rate.

The predicted trajectory, $\hat{Y}$, is considered to be a sum of two parts: a contribution from the kinematic reflex responses, $\hat{Y}_{MA}$, and a contribution from the unperturbed gait (baseline trajectory, $\hat{Y}_B$). This results in a step trajectory Y(t).

In a concrete implementation example, both models ($Y^{\wedge}_\perp MA, Y^{\wedge}_\perp B$) may be continuously updated. By disabling the stimulation with a five step interval, a baseline-step may be acquired and used as an updated $\hat{Y}_B$, by letting $\hat{Y}_B=Y$. In the other four controller-corrected-steps, the reflex response model ($\hat{Y}_{MA}$) is updated by first calculating the reflex response as the error between the present step and the latest baseline-step ($e_1=Y-\hat{Y}_B$) and then use a simple MA approach for estimating $\hat{Y}_{MA}$ at time t. The MA of the last five steps corresponding to the same input parameters can then be calculated.

At the end of each swing phase, immediately after the update of the adaptive neuro-muscular plant model, the controller algorithm calculates the predicted step ($\hat{Y}$) for all combinations of stimulation site and phase based on the adaptive neuro-muscular plant model.

Additional features that may be present in one or more of the embodiments described herein, in particular regarding the implementation of the control algorithm may be found in any one or more of the following references, all of which are hereby expressly incorporated by reference in their entireties:

Ph.D. thesis: "Modulation of the nociceptive withdrawal reflex and its use in rehabilitation of gait of stroke patients", J. Emborg, Center for Sensory-Motor Interaction (SMI), Department of Health Science and Technology, Aalborg University, 2009

"Withdrawal reflex responses evoked by repetitive painful stimulation delivered on the sole of the foot during late stance: site, phase, and frequency modulation", E. G. Spaich, J. Emborg, T. Collet, L. Arendt-Nielsen, and O. K. Andersen, Exp. Brain Res., vol. 194, no. 3, pp. 359-368, April 2009

"Withdrawal reflexes examined during human gait by ground reaction forces: site and gait phase dependency", J. Emborg, E. G. Spaich, and O. K. Andersen, Med. Biol. Eng. Comput. 2009; vol. 4, pp. 29-39, January 2009

"Novel method exploiting the nociceptive withdrawal reflexes in rehabilitation of hemiplegic gait" Emborg, J.; Bendtsen, J. D.; Spaich, E. G.; Andersen, O. K., 2009. s. 84-87 World Congress on Medical Physics and Biomedical Engineering, Munich, Germany, 7-12 Sep. 2009, International Federation for Medical and Biological Engineering Proceedings. 25. IX Accordingly, embodiments described herein provide a device and method for gait training, such as for rehabilitation of a person after a stroke. The devices comprise a stimulator, preferably electric stimulator, for provoking a spinal cord withdrawal reflex in a person (also referred to as a "subject" in some contexts though it should be understood that the term subject also encompasses mammals as a class including, but not limited to, humans) by stimulation of the person's or subject's foot in response to a control signal. Hereby, the person's leg will move and initiate a gait swing. A sensor is placed to sense movement of the leg and provide a feedback signal accordingly. A processor unit with a processor runs a control algorithm which calculates the control signal in response to the feedback signal. Thus, the method is based on a closed-loop design, and the control signal is preferably calculated for each walking step, and it is preferably based on the feedback signal obtained from the preceding walking step. Hereby reflex habituation can be accounted for. Preferably, the stimulator has a plurality of stimulator channels with electrodes placed on different sites distributed on the sole of the foot and on the heel. The feedback signal may be based on accelerometer(s), and/or gyroscope(s), and/or goinometer(s) positioned on the leg and/or foot, e.g. partly or fully integrated in an in-sole for a shoe etc.

Although the present invention has been described in connection with preferred embodiments, it is not intended to be limited to the specific form set forth herein. Rather, the scope of the present invention is limited only by the accompanying claims.

In this section, certain specific details of the disclosed embodiments are set forth for purposes of explanation rather than limitation, so as to provide a clear and thorough understanding of the present invention. However, it should be understood readily by those skilled in this art, that the present invention may be practised in other embodiments which do not conform exactly to the details set forth herein, without departing significantly from the spirit and scope of this disclosure. Further, in this context, and for the purposes of brevity and clarity, detailed descriptions of well-known device, circuits and methodology have been omitted so as to avoid unnecessary detail and possible confusion.

In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Reference signs are included in the claims however the inclusion of the reference signs is only for clarity reasons and should not be construed as limiting the scope of the claims.

What is claimed is:

1. A device for gait training of a subject comprising:
 a stimulator configured to generate a stimulation on a foot of the subject in response to a control signal, wherein the stimulation is arranged to provoke a spinal cord withdrawal reflex in the subject so as to cause the person's leg to move,
 a sensor configured to sense a parameter representative of a movement of the subject's leg and to generate a feedback signal accordingly, and
 a processor unit operationally connected to the stimulator and the sensor, the processor unit comprising a processor running a control algorithm so as to generate the control signal in response to the feedback signal.

2. The device according to claim 1, wherein the stimulator comprises an electric stimulator configured to generate an electric stimulation on the person's foot and thereby provoke the spinal cord reflex.

3. The device according to claim 1, wherein the control algorithm is arranged to vary the control signal in response to the feedback signal so as to optimize a quality of gait.

4. The device according to claim 1, wherein the stimulator comprises a plurality of individually controllable stimulators spatially distributed to provide stimulation on different positions on the subject's foot.

5. The device according to claim 4, wherein the stimulator comprises at least a stimulator configured to stimulate the subject's heel and a stimulator arranged to stimulate a position on the subject's sole of the foot.

6. The device according to claim 5, wherein the stimulator comprises a plurality of stimulator channels arranged to stimulate different sites on the subject's foot.

7. The device according to claim 1, wherein the control algorithm and the stimulator are arranged so as to vary at least one of: stimulation intensity, stimulation duration, stimulation timing in the gait cycle, or stimulation site in response to the feedback signal.

8. The device according to claim 7, wherein the control algorithm is arranged to generate the control signal in response to the feedback signal by selecting between one of a plurality of predetermined stimulation options selected from the group consisting of stimulation with different stimulation intensities, different stimulation timing in the gait cycle, different stimulation duration, and different stimulation sites.

9. The device according to claim 8, wherein selection between predetermined stimulation options comprises selecting between a number of predefined sets of stimulation parameters stored in memory, and wherein each of said predefined sets of stimulation parameters have been evaluated with respect to a target measure, so as to allow a selection based on this target measure.

10. The device according to claim 9, wherein the predefined sets of stimulation parameters comprises at least the variables of onset of gait cycle and stimulation site.

11. The device according to claim 10, wherein the predefined sets of stimulation parameters comprises at least twelve sets with four stimulation sites on the person's foot, and three onset times between heel-off and toe-off.

12. The device according to claim 9, comprising calculating an estimated error from a target trajectory for each of the predefined sets of stimulation parameters, and selecting the predefined set of stimulation parameters resulting in a minimal error from the target trajectory.

13. The device according to claim 1, wherein the processor unit is configured to calculate the control signal for each walking step of the person.

14. The device according to claim 13, wherein the processor unit is configured to calculate the control signal for a walking step based on the feedback signal received during at least one previous walking step or during the preceding walking step.

15. The device according to claim 14, wherein the control algorithm is arranged to calculate an estimated deviation from a predetermined target trajectory for a walking step based on the feedback signal from at least one previous walking step.

16. The device according to claim 1, wherein the processor unit is implemented as a portable unit, which, optionally, may be attached to a part of the subject's clothes.

17. The device according to claim 1, comprising a second stimulator arranged for stimulation on the subject's opposite foot, and a second sensor arranged to sense a second parameter representative of a position of the subject's opposite leg, and, wherein the processor unit is arranged to generate a second control signal to the second stimulator in response to a second feedback signal from the second sensor, so as to provoke movement of both legs of the subject.

18. A method of rehabilitation therapy of a gait impaired patient, comprising:
sensing a parameter representative of a position of the patient's leg, and
applying a simulation on the patient's foot in order to provoke a spinal cord withdrawal reflex causing the patient's leg to move, wherein the stimulation is determined in response to said parameter representative of the position of the patient's leg.

19. A computer executable program code, embodied on a non-transitory medium, arranged to cause a computer device to generate a control signal to a stimulator in response to a feedback signal from a sensor so as to perform the method according to claim 18.

* * * * *